(12) United States Patent
Noshi et al.

(10) Patent No.: US 10,185,044 B2
(45) Date of Patent: Jan. 22, 2019

(54) PHOTON-COUNTING APPARATUS

(71) Applicant: Toshiba Medical Systems Corporation, Otawara-shi (JP)

(72) Inventors: Yasuhiro Noshi, Otawara (JP); Shuya Nambu, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 450 days.

(21) Appl. No.: 14/956,983

(22) Filed: Dec. 2, 2015

(65) Prior Publication Data

US 2016/0081637 A1 Mar. 24, 2016

Related U.S. Application Data

(63) Continuation of application No. PCT/JP2014/064489, filed on May 30, 2014.

(30) Foreign Application Priority Data

Jun. 6, 2013 (JP) ................................. 2013-119708

(51) Int. Cl.
  *A61B 6/00* (2006.01)
  *G01T 1/24* (2006.01)
  *H01L 27/146* (2006.01)
  (Continued)

(52) U.S. Cl.
  CPC .............. *G01T 1/247* (2013.01); *A61B 6/032* (2013.01); *A61B 6/4241* (2013.01); *A61B 6/482* (2013.01);
  (Continued)

(58) Field of Classification Search
  CPC ........... A61B 6/00; A61B 6/42; A61B 6/4208; A61B 6/4241; A61B 6/48; A61B 6/482;
  (Continued)

(56) References Cited

U.S. PATENT DOCUMENTS 6,362,482 B1 * 3/2002 Stettner ................. G01T 1/1644
  250/370.01
2007/0290142 A1 12/2007 Du et al.
  (Continued)

FOREIGN PATENT DOCUMENTS

JP 2007-333734 12/2007
JP 2009-078143 4/2009
  (Continued)

OTHER PUBLICATIONS

International Search Report dated Sep. 2, 2014 in PCT/JP2014/064489 filed May 30, 2014 (with English translation).
Written Opinion dated Sep. 2, 2014 in PCT/JP2014/064489 filed May 30, 2014.

*Primary Examiner* — Anastasia Midkiff
(74) *Attorney, Agent, or Firm* — Oblon, McClelland, Maier & Neustadt, L.L.P.

(57) ABSTRACT

According to one embodiment, a photon-counting apparatus includes an X-ray tube, an X-ray detector, a support mechanism, setting circuitry and data acquisition circuitry. The X-ray detector is configured to repetitively detect an X-ray photon generated by the X-ray tube, and repetitively generate an electrical signal corresponding to the repetitively detected X-ray photon. The support mechanism is configured to support the X-ray tube to be rotatable about a rotation axis. Setting circuitry configured to set one of a time length of a readout period and a readout cycle per unit time for the electrical signal. Data acquisition circuitry is configured to count a count number of electrical signals from the X-ray detector in accordance with the set one of the time length and readout cycle.

16 Claims, 12 Drawing Sheets

(51) Int. Cl.
*H01L 27/148* (2006.01)
*A61B 6/03* (2006.01)
*G01T 1/29* (2006.01)

(52) U.S. Cl.
CPC ...... *G01T 1/2985* (2013.01); *H01L 27/14658* (2013.01); *H01L 27/14806* (2013.01)

(58) Field of Classification Search
CPC .. A61B 6/484; G01T 1/00; G01T 1/16; G01T 1/24; G01T 1/247; G01T 1/2985; H01L 27/144; H01L 27/146; H01L 27/14601; H01L 27/14658; H01L 27/148; H01L 27/14806; G01N 23/00; G01N 23/02; G01N 2223/00; G01N 2223/40; G01N 2223/401; G01N 2223/423; G01N 2223/50
See application file for complete search history.

(56) References Cited

U.S. PATENT DOCUMENTS

| | | |
|---|---|---|
| 2009/0080601 A1 | 3/2009 | Tkaczyk et al. |
| 2010/0213353 A1* | 8/2010 | Dierickx ............... G01T 1/17 250/214 R |
| 2011/0036988 A1* | 2/2011 | Campbell ............. G01T 1/026 250/370.07 |
| 2012/0228511 A1 | 9/2012 | Moteki et al. |
| 2014/0183371 A1* | 7/2014 | Roessl .................. G01T 1/241 250/370.09 |

FOREIGN PATENT DOCUMENTS

| | | |
|---|---|---|
| JP | 2012-189391 | 10/2012 |
| JP | 2013-007585 | 1/2013 |

* cited by examiner

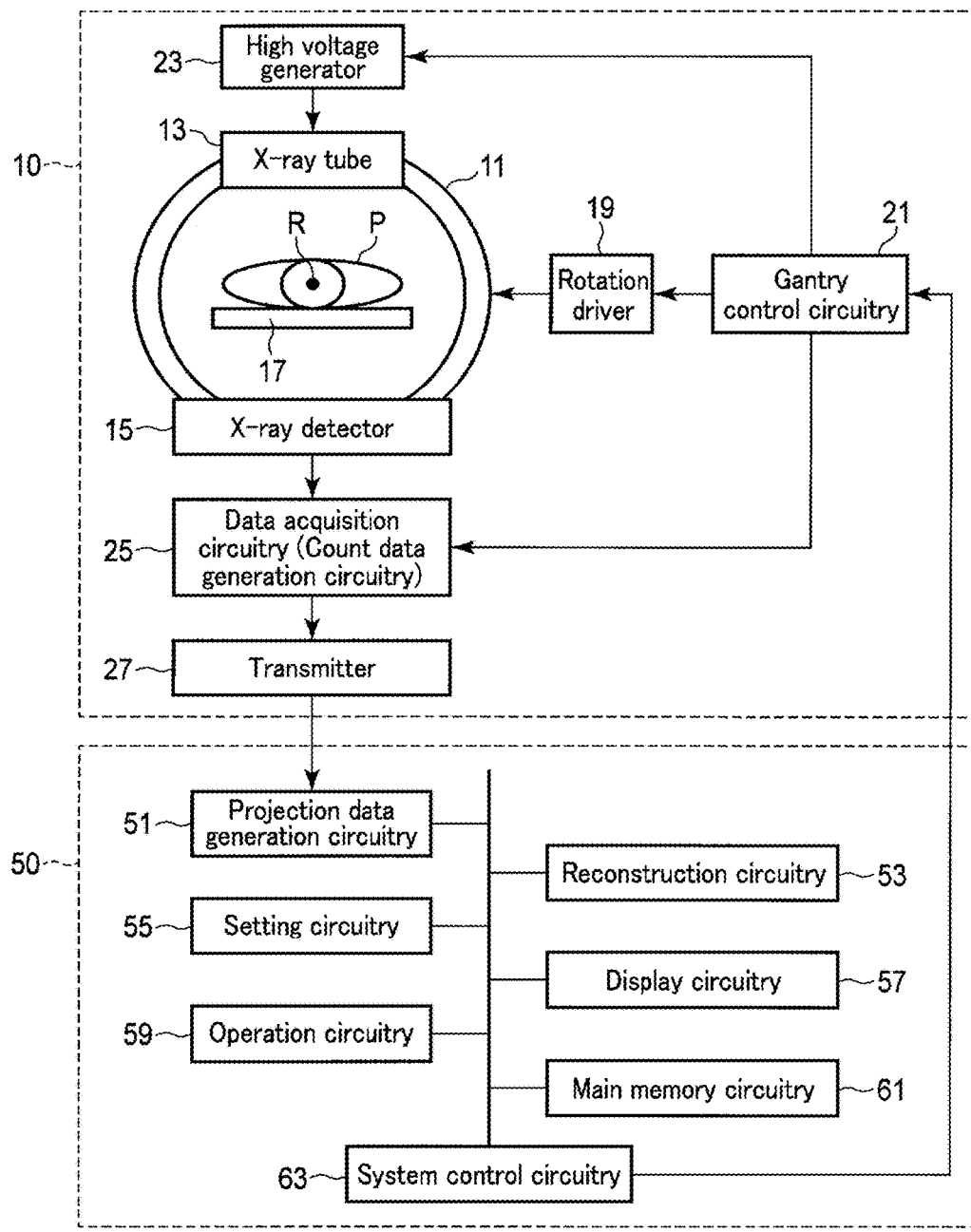
F I G. 1

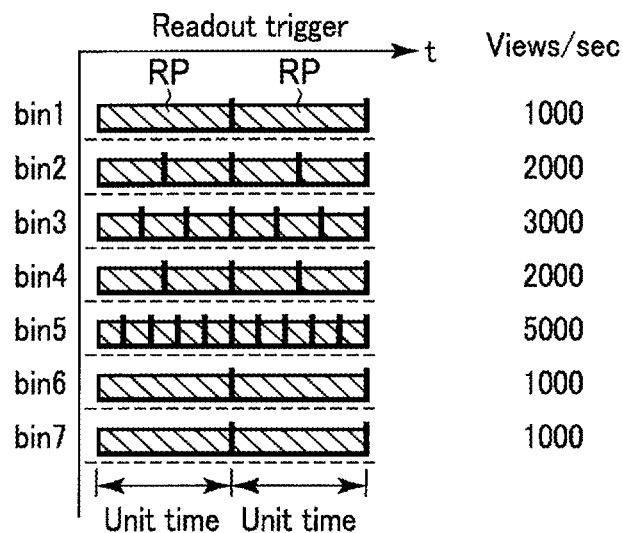
F I G. 4B
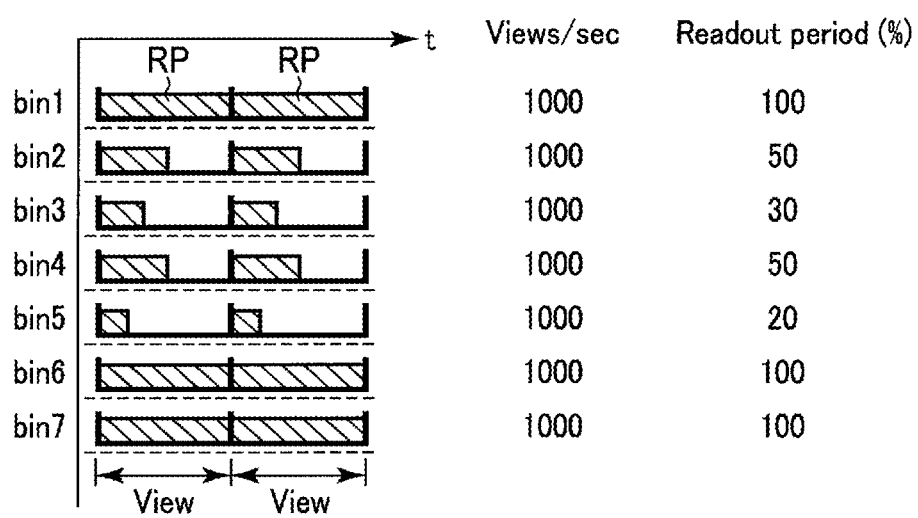
F I G. 5

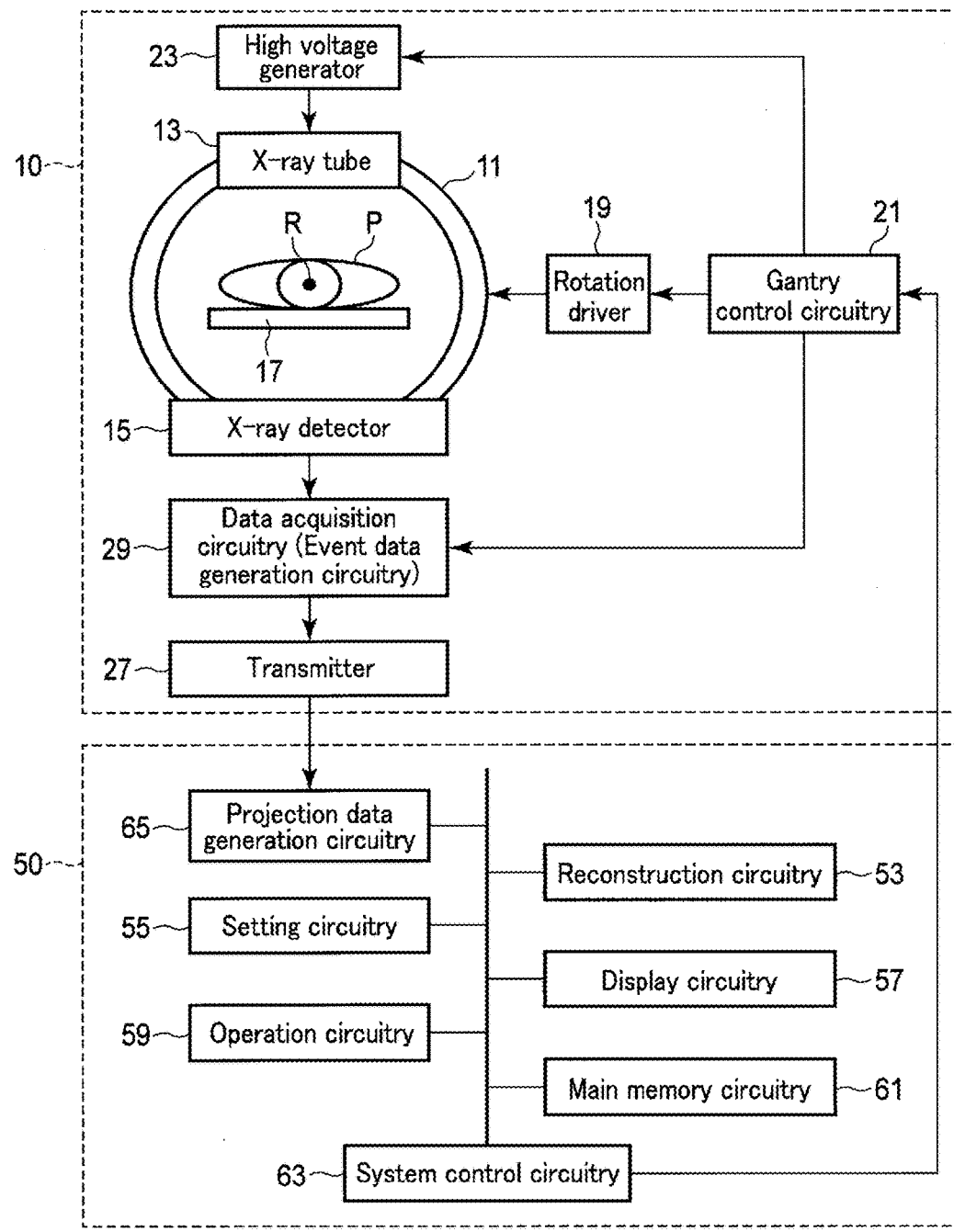
F I G. 10

| | Detection time (t) | Energy (E) | Channel (Ch) | Row (row) |
|---|---|---|---|---|
| Event1 | t1 | E1 | Ch1 | row1 |
| Event2 | t2 | E2 | Ch2 | row2 |
| ⋮ | | | | |
| | | | | |

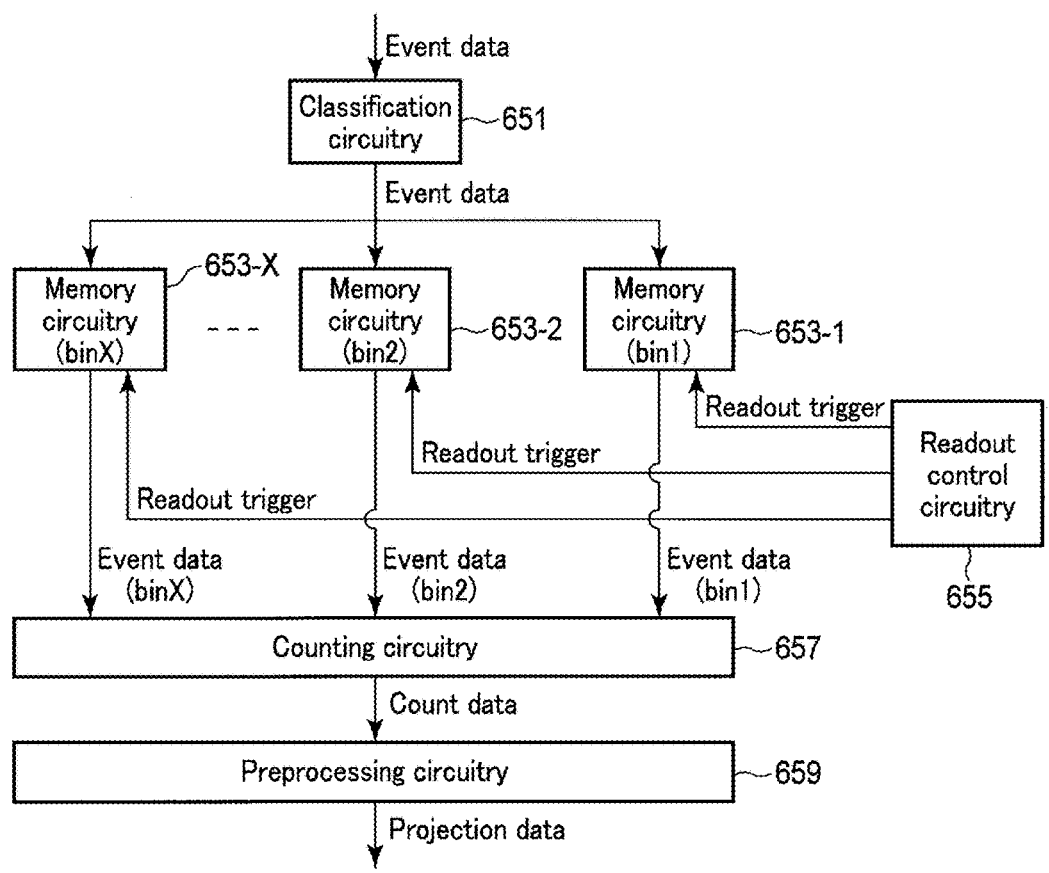
F I G. 13

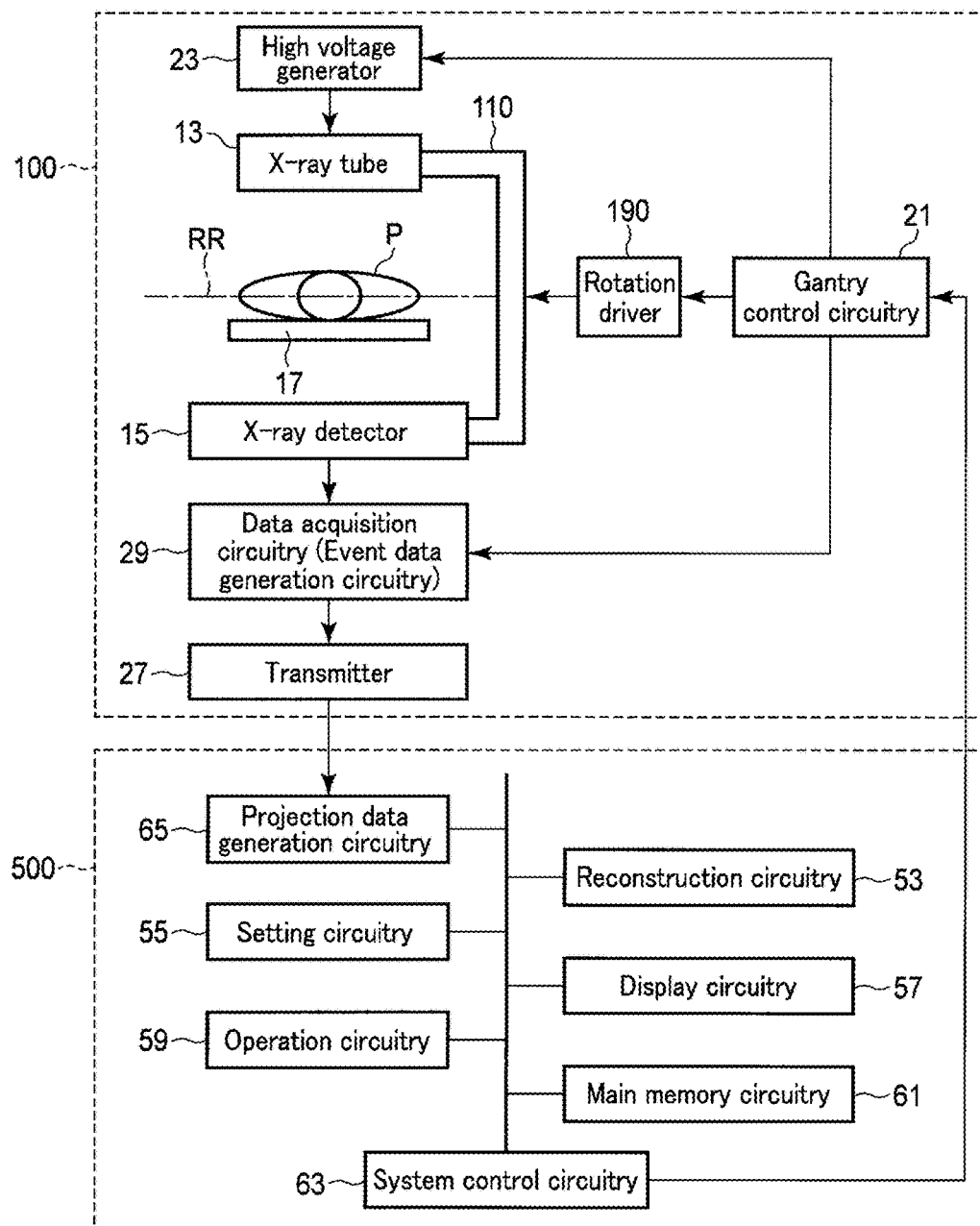
F I G. 14

US 10,185,044 B2

PHOTON-COUNTING APPARATUS

CROSS-REFERENCE TO RELATED APPLICATIONS

This application is a Continuation Application of PCT application No. PCT/JP2014/064489, filed on May 30, 2014, and is based upon and claims the benefit of priority from Japanese Patent Application No. 2013-119708, filed on Jun. 6, 2013, the entire contents of which are incorporated herein by reference.

FIELD

Embodiments described herein relate generally to a photon-counting apparatus.

BACKGROUND

A photon-counting CT (Computed Tomography) apparatus that can classify the energies of X-ray photons into a plurality of energy bands (to be referred to as energy bins hereinafter) has been studied. The number of X-ray photons entering an X-ray detector is different between the energy bins. An overflow readily occurs in an energy bin in which the number of incident photons per unit time is large, in comparison with an energy bin in which the number of incident photons per unit time is small. If the cycle of the readout period is shortened to prevent the generation of the overflow, the count number of X-ray photons in an energy bin in which the number of incident photons per unit time is small cannot be satisfactorily ensured. If the count number is satisfactorily ensured, an overflow occurs in an energy bin in which the number of incident photons per unit time is large.

BRIEF DESCRIPTION OF THE DRAWINGS

FIG. 1 is a block diagram showing the arrangement of a photon-counting CT apparatus according to the first embodiment.

FIG. 4B is a graph showing a readout period set by the setting circuitry in FIG. 1 for each energy bin, and is a graph showing an example of the readout period for each energy bin in the case of FIG. 4A.

FIG. 5 is a view showing another example of a readout period RP for each energy bin in the case of FIG. 4A.

FIG. 10 is a block diagram showing the arrangement of a photon-counting CT apparatus according to the second embodiment.

FIG. 13 is a block diagram showing an example of the arrangement of projection data generation circuitry in FIG. 10.

FIG. 14 is a block diagram showing the arrangement of a photon-counting XR apparatus according to a modification of the second embodiment.

DETAILED DESCRIPTION

Figure 2:
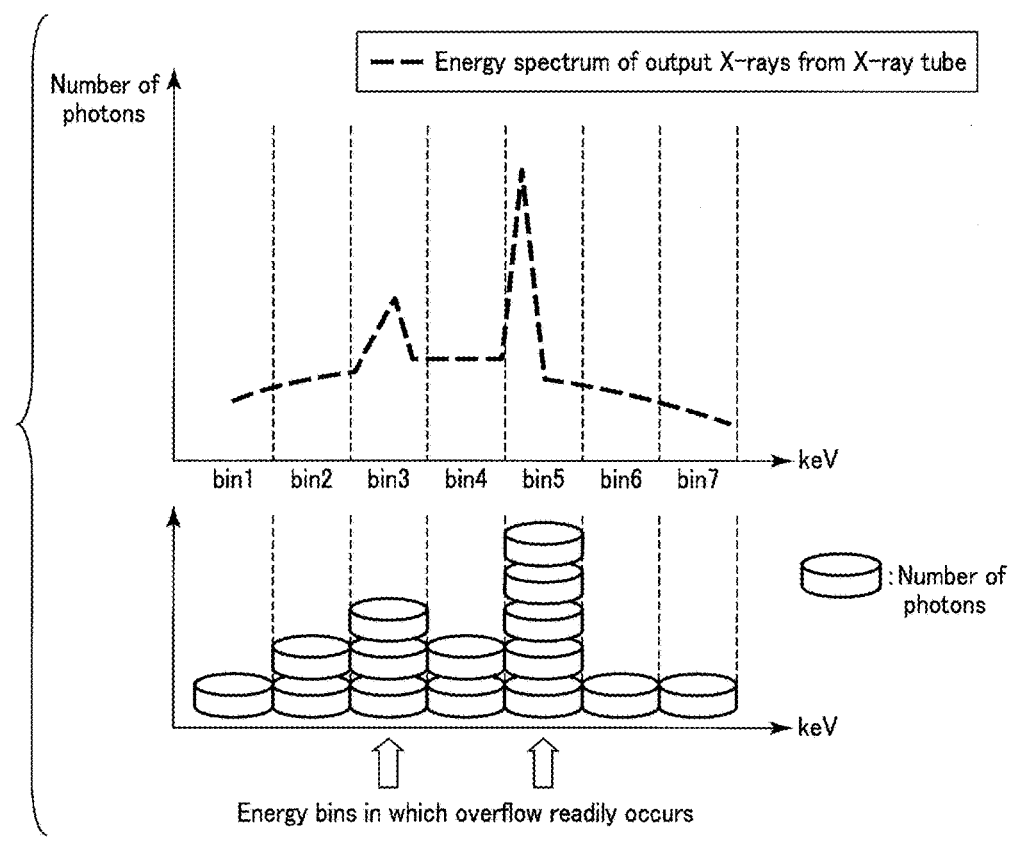
FIG. 2 is a graph showing the relationship between the energy bin and the number of photons in the energy spectrum of X-ray photons generated by an X-ray tube in FIG. 1.

In general, according to one embodiment, a photon-counting apparatus includes an X-ray tube, an X-ray detector, a support mechanism, setting circuitry and data acquisition circuitry. The X-ray tube is configured to generate an X-ray. The X-ray detector is configured to repetitively detect an X-ray photon generated by the X-ray tube, and repetitively generate an electrical signal corresponding to the repetitively detected X-ray photon. The support mechanism is configured to support the X-ray tube to be rotatable about a rotation axis. Setting circuitry configured to set one of a time length of a readout period and a readout cycle per unit time for the electrical signal based on a reference count number for each of a plurality of energy bands concerning X-rays generated from the X-ray tube. Data acquisition circuitry is configured to count a count number of electrical signals from the X-ray detector in accordance with the set one of the time length and readout cycle for each of the plurality of energy bands.

A photon-counting apparatus according to an embodiment will now be described with reference to the accompanying drawings.

The photon-counting apparatus according to this embodiment is applicable to either of an X-ray CT type apparatus (to be referred to as a photon-counting CT apparatus hereinafter) and an X-ray imaging type apparatus (to be referred to as a photon-counting XR apparatus hereinafter). The photon-counting apparatus according to this embodiment will be explained in detail by exemplifying the photon-counting CT apparatus.

The photon-counting CT apparatus according to this embodiment is an X-ray computed tomography apparatus having an arrangement in which data acquisition in a photon-counting mode can be executed. X-ray detectors are, for example, a scintillator type (combination of a scintillator and photoelectric element) and a semiconductor detector type, and this embodiment is applicable to any type. However, the following description assumes that the X-ray detector is a semiconductor detector suitable for the photon-counting mode.

Various types of photon-counting CT apparatuses can be assumed, including a rotate/rotate-type apparatus in which an X-ray tube and an X-ray detector integrally rotate around an object, and a stationary/rotate-type apparatus in which many X-ray detection elements arrayed in a ring are fixed and only an X-ray tube rotates around an object. This embodiment is applicable to any type. However, the following explanation assumes that the photon-counting CT apparatus is a rotate/rotate-type apparatus.

As the data acquisition method in the photon-counting CT apparatus, there are known a count mode in which the count number of X-ray photons in each view is counted, and a list mode in which the energy value of each X-ray photon is recorded in time series. This embodiment is applicable to any type. A photon-counting CT apparatus in the count mode will be explained in the first embodiment, and a photon-counting CT apparatus in the list mode will be explained in the second embodiment.

(First Embodiment)

FIG. 1 is a block diagram showing the arrangement of a photon-counting CT apparatus according to the first embodiment.

As shown in FIG. 1, an X-ray computed tomography apparatus 1 includes a gantry 10 and a console 50.

The gantry 10 supports a cylindrical rotating frame 11 to be rotatable about a rotation axis R. An X-ray tube 13 and an X-ray detector 15 are attached to the rotating frame 11 so as to face each other with respect to the rotation axis R. The opening of the rotating frame 11 is set to an FOV (Field Of View). A top 17 is positioned inside the opening of the rotating frame 11. An object P is placed on the top 17. The top 17 is moved so that the imaging portion of the object P placed on the top 17 is included in the FOV. The rotating frame 11 receives power from a rotation driver 19 and rotates about the rotation axis R at a predetermined angular velocity. The rotation driver 19 generates power for rotating the rotating frame 11 in accordance with a driving signal from gantry control circuitry 21.

The X-ray tube 13 generates X-rays upon receiving application of a high voltage and supply of a filament current from a high voltage generator 23. The generated X-rays have an energy spectrum corresponding to the material of an anode installed in the X-ray tube 13. The high voltage generator 23 applies, to the X-ray tube 13, a high voltage complying with a control signal from the gantry control circuitry 21 and supplies, to the X-ray tube 13, a filament current complying with a control signal from the gantry control circuitry 21.

The X-ray detector 15 detects X-ray photons generated by the X-ray tube 13. The X-ray detector 15 includes a plurality of X-ray detection elements arrayed two-dimensionally. For example, the plurality of X-ray detection elements are arrayed along an arc centered at the rotation axis R of the rotating frame 11. The array direction of the X-ray detection elements along the arc is called a channel direction. The plurality of X-ray detection elements arrayed in the channel direction are called an X-ray detection element row. A plurality of X-ray detection element rows are arrayed in a row direction along the rotation axis R.

Each X-ray detection element detects X-ray photons from the X-ray tube 13, and generates an electrical pulse (electrical signal) corresponding to the energy of the detected X-ray photons. More specifically, the X-ray detection element is constituted by a semiconductor diode formed by attaching electrodes to the two ends of a semiconductor. X-ray photons that have entered the semiconductor are converted into electron-hole pairs. The number of electron-hole pairs generated by the entrance of one X-ray photon depends on the energy of the incident X-ray photon. Electrons and holes are attracted by the pair of electrodes formed at the two ends of the semiconductor. The pair of electrodes generates an electrical pulse having a peak value corresponding to the charges of electron-hole pairs. One electrical pulse has a peak value corresponding to the energy of the incident X-ray photon. A semiconductor material according to this embodiment is preferably a substance that can efficiently convert X-ray photons into electron-hole pairs and has a relatively large atomic number. Known examples of the semiconductor material suitable for photon-counting CT are CdTe and CdZnTe.

Data acquisition circuitry 25 generates count data representing a count number in each view, based on electrical pulses from the X-ray detector 15 for each of a plurality of energy bins in accordance with a control signal from the gantry control circuitry 21. A transmitter 27 transmits the count data to the console 50.

The gantry control circuitry 21 generally controls various devices mounted on the gantry 10 in accordance with an instruction from system control circuitry 63 in the console 50. For example, the gantry control circuitry 21 controls the rotation driver 19, the high voltage generator 23, and the data acquisition circuitry 25. More specifically, the gantry control circuitry 21 controls the rotation driver 19 to rotate the rotating frame 11 at a predetermined angular velocity. The gantry control circuitry 21 controls the high voltage generator 23 to generate X-rays corresponding to predetermined X-ray conditions from the X-ray tube 13. The gantry control circuitry 21 controls the data acquisition circuitry 25 to acquire count data. More specifically, the gantry control circuitry 21 controls the data acquisition circuitry 25 to acquire count data for each of a plurality of energy bins in accordance with the time length or cycle of a readout period set by setting circuitry 55 (to be described later) for each of the plurality of energy bins. The cycle of the readout period will also be called a readout cycle.

The console 50 includes projection data generation circuitry 51, reconstruction circuitry 53, the setting circuitry 55, display circuitry 57, operation circuitry 59, main memory circuitry 61, and the system control circuitry 63. The projection data generation circuitry 51 generates projection data based on count data transmitted from the transmitter 27 for each of the plurality of energy bins. The reconstruction circuitry 53 reconstructs image data concerning an object based on projection data concerning a predetermined energy bin out of the plurality of energy bins. The setting circuitry 55 sets the time length or cycle of the readout period per unit time for each of the plurality of energy bins. The display circuitry 57 displays image data generated by the reconstruction circuitry 53, and the like on a display device. The operation circuitry 59 accepts various instructions and information inputs from a user via an input device. The main memory circuitry 61 stores count data, projection data, and image data. Also, the main memory circuitry 61 stores control programs. The system control circuitry 63 reads out a control program stored in the main memory circuitry 61, loads it into a memory, and controls each unit in accordance with the loaded control program.

An example of the operation of the photon-counting CT apparatus according to the first embodiment will be described next.

First, the relationship between the energy bin and the number of photons will be explained with reference to FIG. 2. FIG. 2 is a graph showing the relationship between the energy bin and the number of photons in the energy spectrum of X-ray photons generated by the X-ray tube 13. Note that FIG. 2 shows an energy spectrum when the anode in the X-ray tube 13 is tungsten. In FIG. 2, the ordinate is defined as the number of photons, and the abscissa is defined as the energy component [keV]. In FIG. 2, seven energy bins bin1 to bin7 are set. Each energy bin is defined by the energy center value and energy width of the energy bin. The number of energy bins, the energy center value, and the energy width can be arbitrarily set by the user via the operation circuitry 59.

As shown in FIG. 2, X-rays generated by the X-ray tube 13 are continuous X-rays and include a plurality of energy components. In photon-counting CT, the number of X-ray photons is counted for each of the plurality of energy bins in the energy spectrum. The number of X-ray photons entering the X-ray detector 15 differs between the energy bins. An overflow readily occurs in an energy bin in which the number of incident photons per unit time is large, in comparison with an energy bin in which the number of incident photons per unit time is small. For example, the number of photons is larger in bin3 and bin5 than in the remaining energy bins, and an overflow readily occurs. If the cycle of the readout period is shortened to prevent the generation of the overflow, the count number of X-ray photons in an energy bin in which the number of incident photons per unit time is small cannot be satisfactorily ensured. If the count number is satisfactorily ensured, an overflow occurs in an energy bin in which the number of incident photons per unit time is large.

The photon-counting CT apparatus according to the first embodiment sets the time length or cycle of a readout period suited to each energy bin for each of the plurality of energy bins, thereby reducing the overflow generation probability while ensuring the number of photons suited to each energy bin.

Figure 3:
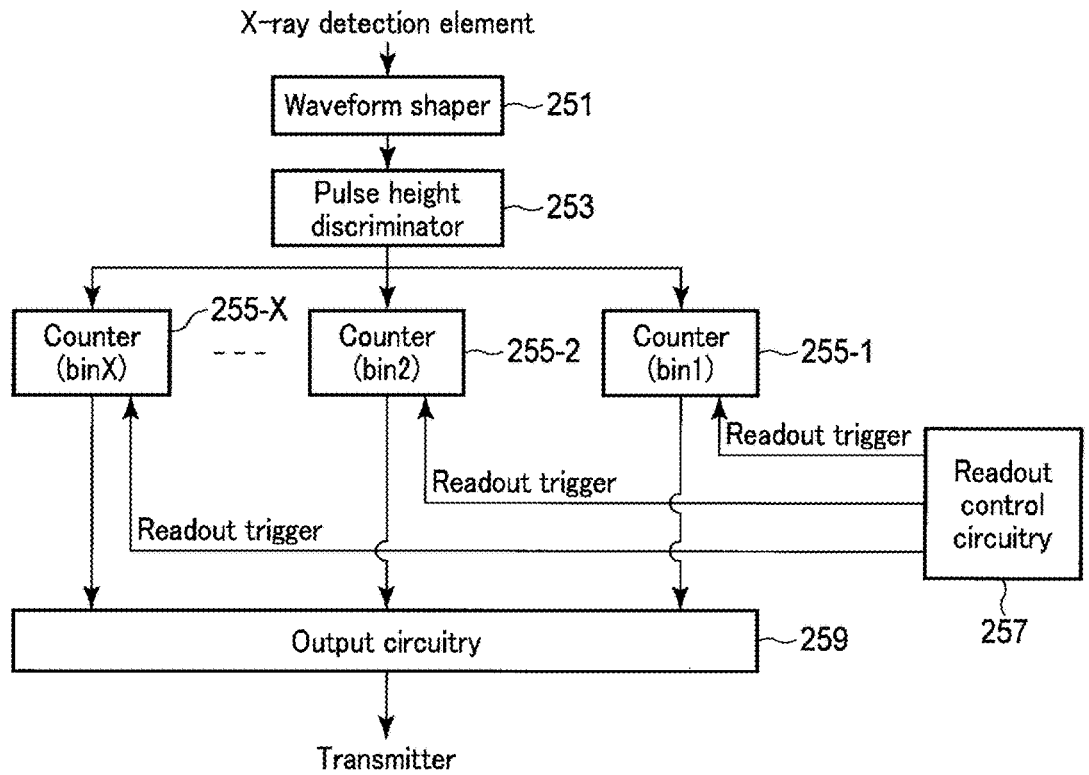
FIG. 3 is a block diagram showing an example of the arrangement of one channel of data acquisition circuitry in FIG. 1.

First, the arrangement and operation of the data acquisition circuitry 25 will be described. The data acquisition circuitry 25 has readout channels by the number of channels corresponding to the number of X-ray detection elements. The plurality of readout channels are parallelly implemented on an integrated circuit such as an ASIC (Application Specific Integrated Circuits). FIG. 3 is a block diagram showing an example of the arrangement of one channel of the data acquisition circuitry 25. As shown in FIG. 3, the data acquisition circuitry 25 includes, for each of the plurality of readout channels, a waveform shaper 251, a pulse height discriminator 253, counters 255, readout control circuitry 257, and output circuitry 259. The waveform shaper 251, the pulse height discriminator 253, the counters 255, the readout control circuitry 257, and the output circuitry 259 are implemented on an integrated circuit such as an ASIC.

The waveform shaper 251 shapes the waveform of an electrical pulse from the X-ray detection element. The pulse height discriminator 253 is connected to the waveform shaper 251. The pulse height discriminator 253 discriminates the peak value of an electrical pulse from the waveform shaper 251, i.e., the energy of X-ray photons detected by the X-ray detection element. The counters 255 are connected to the pulse height discriminator 253 by a number corresponding to the number of energy bins. For example, when X energy bins are set, the pulse height discriminator 253 determines, by threshold processing, one of the X energy bins to which the energy of X-ray photons detected by the X-ray detection element belongs. Then, the pulse height discriminator 253 outputs an electrical pulse corresponding to the energy bin to which the X-ray photons belong, to the counter 255 corresponding to the energy bin to which the X-ray photons belong. The threshold for pulse height discrimination is set in advance in accordance with the number of energy bins. For example, when seven energy bins are set, the seven counters 255 are connected to the pulse height discriminator 253, as shown in FIG. 2.

When the pulse height discriminator 253 determines that the energy of X-ray photons detected by the X-ray detection element has a peak value corresponding to an energy bin X, the pulse height discriminator 253 outputs an electrical pulse to the counter 255-X corresponding to the energy bin X.

The plurality of counters 255 are connected to the pulse height discriminator 253. Each counter 255 counts electrical pulses from the pulse height discriminator 253 in the time length or cycle of the readout period under the control of the readout control circuitry 257. In response to receiving a readout trigger from the readout control circuitry 257, the counter 255 starts counting of electrical pulses input from the pulse height discriminator 253. Every time an electrical pulse is input, the counter 255 increments by one a count number stored in an internal memory. In response to receiving the next readout trigger, the counter 255 reads out data (count data) of the count number stored in the internal memory, and resets the data of the count number in the internal memory to an initial value (e.g., 0).

The internal memory of the counter 255 has the upper limit of the capacity for the count number. A case will be examined, in which readout is performed at the same timing for all counters concerning a plurality of energy bins, as in the related art. When the time length or cycle of the readout period is relatively short, a satisfactory count number cannot be obtained for an energy bin in which the number of incident photons per unit time is small, like energy bin 1, and this may cause an image artifact. When the time length or cycle of the readout period is relatively long, the internal memory of the counter reaches the upper limit value of counting for an energy bin in which the number of incident photons per unit time is large, like energy bin 5, and an overflow (counting loss) occurs.

Figure 4A:
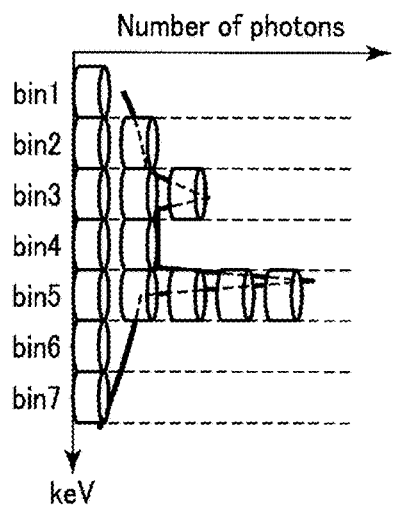
FIG. 4A is a graph showing a readout period set by setting circuitry in FIG. 1 for each energy bin, and is a graph showing the relationship between the energy bin and the number of photons in FIG. 2.

In this embodiment, the setting circuitry 55 sets the time length or cycle of the readout period for data (count data) of a count number from the counter 255 in accordance with the number of incident photons per unit time in each energy bin. FIGS. 4A and 4B are graphs showing the readout period set by the setting circuitry 55 for each energy bin. FIG. 4A is a graph showing the relationship between the energy bin and the number of photons in FIG. 2. FIG. 4B is a graph showing an example of the readout period for each energy bin in the case of FIG. 4A. Each black vertical line in FIG. 4B indicates a readout trigger. The time interval between readout triggers is conventionally called a view in the CT field. The time interval between readout triggers will also be called a view depending on the situation. A readout period RP of data is set for each view. In FIG. 4B, the readout period RP is set throughout the entire period of each view. That is, the time length of the readout period RP is set so that the time length of the readout period RP and that of the view coincide with each other. The number of generated readout triggers per unit time is defined by the readout frequency (views/sec) of count data from the counter 255, in other words, the cycle of the readout period RP. The readout cycle (view cycle) can also be rewritten into the readout speed of count data from the counter 255.

As shown in FIGS. 4A and 4B, the setting circuitry 55 sets, for each of the plurality of energy bins, the cycle of the readout period RP of count data from the counter 255, in other words, the readout trigger generation cycle in accordance with the number of incident photons per unit time in each energy bin. The setting circuitry 55 sets the cycle of the readout period RP for an energy bin in which the number of incident X-ray photons per unit time is large, to have a value smaller than the value of the cycle of the readout period RP for an energy bin in which the number of incident X-ray photons per unit time is small. For example, the cycle of the readout period RP for energy bin 1 is set to perform readout 1,000 times per sec (1,000 views/sec). Energy bin 5 is five times larger in the number of incident photons than energy bin 1. Thus, the cycle of the readout period RP for energy bin 5 is preferably set to perform readout 5,000 times per sec (5,000 views/sec). The first readout trigger generation times of all the energy bins are set to be the same timing. The cycles of the readout periods RP of all the energy bins are preferably set to be integer multiples of the basic clock generation cycle. The setting of the cycle of the readout period RP is performed at the time of a scan plan. Data of the set cycle of the readout period RP for each energy bin is transmitted to the readout control circuitry 257 via the gantry control circuitry 21.

Referring back again to FIG. 3, the data acquisition circuitry 25 will be explained. As shown in FIG. 3, the readout control circuitry 257 transmits a readout trigger to the counter 255 corresponding to each energy bin in accordance with the cycle of a readout period set for this energy bin. In response to receiving the readout trigger from the readout control circuitry 257, each counter 255 counts electrical pulses input from the pulse height discriminator 253. Every time an electrical pulse is input, the counter 255 increments by one a count number stored in the internal memory. In response to receiving the next readout trigger, the counter 255 reads out data (count data) of the count number stored in the internal memory, and resets the count number stored in the internal memory to an initial value (e.g., 0). The counter 255 starts again counting of electrical pulses from the pulse height discriminator 253. In this manner, the counter 255 repetitively generates count data in every readout period (view). The count data is digital data representing the count number of X-ray photons by each X-ray detection element for each view. For example, when the readout cycle is set, as shown in FIG. 4B, the counter 255-5 corresponding to energy bin 5 performs readout of the count number at a speed five times higher than that of the counter 255-1 corresponding to energy bin 1. The readout count data is supplied to the output circuitry 259.

The output circuitry 259 is connected to the plurality of counters 255. Count data of each view from the corresponding counter 255 is supplied to the output circuitry 259. The output circuitry 259 combines count data from a plurality of readout channels, generating the count data set of each view. The count data set is digital data concerning the count values of X-ray photons for the respective X-ray detection elements mounted in the X-ray detector 15. In other words, the count data set is digital data representing a count value for each combination of the channel number and row number. The output circuitry 259 supplies the count data set to the transmitter 27 in association with the identifier of the energy bin and that of the view.

In the above description, the time length of the readout period is set so that the time length of the readout period and that of the view coincide with each other. However, the embodiment is not limited to this. That is, the time length of the readout period may be set to have a value smaller than that of the time length of each view.

FIG. 5 is a view showing another example of the readout period RP for each energy bin in the case of FIG. 4A. As shown in FIG. 5, the time length of the readout period RP can be arbitrarily set independently of the time length of the view. For example, the readout period RP starts from the readout trigger generation time, and ends after the lapse of a time length set for each energy bin. The upper limit of the time length of the readout period RP is restricted to the time length of the view. The ratio of the time length of the readout period RP to the time length of the view is represented by a percentage. In FIG. 5, the cycles of views in all the energy bins are equal at 1,000 views/sec for descriptive convenience.

As shown in FIG. 5, the setting circuitry 55 sets, for each of the plurality of energy bins, the time length of the readout period RP of count data from the counter 255 in accordance with the number of incident photons per unit time in each energy bin. The setting circuitry 55 sets the time length of the readout period RP for an energy bin in which the number of incident X-ray photons per unit time is large, to have a value smaller than the value of the time length of the readout period RP for an energy bin in which the number of incident X-ray photons per unit time is small. For example, the time length of the readout period RP for energy bin 1 is set to perform readout throughout the entire period of the view (100%). Energy bin 5 is five times larger in the number of incident photons than energy bin 1. Thus, the time length of the readout period RP for energy bin 5 is preferably set to perform readout in only ⅕ of the entire period of the view (20%). The setting of the time length of the readout period RP is performed at the time of a scan plan. Data of the set time length of the readout period RP for each energy bin is transmitted to the readout control circuitry 257 via the gantry control circuitry 21.

In this case, the readout control circuitry 257 transmits a readout trigger to the counter 255 corresponding to each energy bin in accordance with the cycle of the readout period (i.e., the cycle of the view). In response to receiving the readout trigger from the readout control circuitry 257, each counter 255 counts electrical pulses input from the pulse height discriminator 253 for the time length of the readout period set for each energy bin. In response to the lapse of the time length of the readout period or receiving the next readout trigger, the counter 255 reads out data (count data) of the count number stored in the internal memory, and resets the count number stored in the internal memory to an initial value. The counter 255 starts again counting of electrical pulses from the pulse height discriminator 253. In this fashion, the counter 255 repetitively generates count data in every readout period.

The description of the arrangement and operation of the data acquisition circuitry 25 will be ended here. With the above-described arrangement, the data acquisition circuitry 25 can count, for each view in each of the plurality of energy bins, the count number of electrical pulses from the X-ray detector 15 in a readout cycle set for each of the plurality of energy bins.

Note that the user can arbitrarily set which of the time length of the readout period RP and the cycle of the readout period RP is set for each energy bin. By setting the cycle of the readout period RP (i.e., the cycle of the view) for each energy bin, the sampling cycle of count data can be set more finely as the number of incident X-ray photons per unit time is larger. Since the time length of the readout period coincides with that of the view, count data can be acquired successively without temporal interruption. In contrast, when the time length of the readout period RP is set for each energy bin independently of the time length of the view, the sampling cycles of count data can be set to be equal as the number of incident X-ray photons per unit time of sampling of count data increases. Since the time length of the readout period does not always coincide with that of the view, count data can be discretely acquired temporally fragmentarily.

The setting of the number of incident photons per unit time in each energy bin, which is used to set the time length of the readout period or the readout cycle, will be explained. In the following description, the number of incident photons per unit time will be called a reference count number. The reference count number is determined based on actually measured count data acquired by the data acquisition circuitry 25 in imaging (to be referred to as actual imaging hereinafter) used for image reconstruction or scout imaging performed before actual imaging.

The setting of the reference count number using scout imaging will be explained in detail. For example, the setting circuitry 55 sets a reference count number concerning each of the plurality of energy bins based on count data acquired by the data acquisition circuitry 25 in scout imaging. Scout imaging is a method of performing imaging while moving the top 17 in a state in which the angle of the X-ray tube 13 about the rotation axis R is fixed. In scout imaging, the gantry control circuitry 21 positions the X-ray tube 13 at a predetermined rotation angle, controls the high voltage generator 23 and the data acquisition circuitry 25 while moving the top 17, and performs imaging throughout the readout period (view) in scout imaging. The object P is placed on the top 17. For each of the plurality of energy bins, the data acquisition circuitry 25 acquires count data throughout the readout period in scout imaging. The setting circuitry 55 measures a count number concerning the readout period in scout imaging, and divides the count number by the time length of the readout period, thereby calculating a reference count number. A reference count number concerning each of the plurality of energy bins is stored in the main memory circuitry 61. The data resource acquired by scout imaging can be exploited without waste, by using scout imaging for the setting of the readout cycle or the time length of the readout period by the setting circuitry 55.

Next, the setting of the reference count number using actual imaging will be explained. For example, the setting circuitry 55 sets a reference count number concerning each of the plurality of energy bins based on count data concerning the readout period of a predetermined ordinal number that has been acquired by the data acquisition circuitry 25 in actual imaging. In actual imaging, the gantry control circuitry 21 controls the rotation driver 19, the high voltage generator 23, and the data acquisition circuitry 25, and performs imaging throughout a plurality of readout periods. The object P is placed on the top 17. For each of the plurality of energy bins, the data acquisition circuitry 25 acquires count data throughout the plurality of readout periods. The setting circuitry 55 measures a count number concerning the readout period of a predetermined ordinal number, and divides the count number by the time length of the readout period, thereby calculating a reference count number. The readout period of the predetermined ordinal number is arbitrary and is preferably, for example, the first readout period immediately after the start of actual imaging. A reference count number concerning each of the plurality of energy bins is stored in the main memory circuitry 61. By using actual imaging, X-ray conditions concerning a reference count number used to set a readout cycle or the time length of a readout period, and a count number used to reconstruct an image can coincide with each other.

By using actual imaging and scout imaging in this way, an appropriate readout cycle, an appropriate time length of the readout period, or the like complying with the geometry of an object can be set.

In the above example, the reference count number is calculated based on an actually measured count number acquired by imaging the object P. However, the embodiment is not limited to this. For example, the main memory circuitry 61 may store candidate values of a reference count number set in advance for each of the plurality of energy bins. In this case, the candidate values may be any of values actually measured in advance for many unspecified persons, or predicted values calculated by simulation. At this time, the main memory circuitry 61 suffices to store the candidate values of the reference count number of each of the plurality of energy bins for each imaging region or each imaging substance. In this case, the setting circuitry 55 reads out, from the main memory circuitry 61 for each of the plurality of energy bins, candidate values corresponding to the imaging region or the imaging substance input via the operation circuitry 59. The setting circuitry 55 sets the readout candidate values concerning the plurality of energy bins in reference count numbers concerning the plurality of energy bins, respectively. Then, the setting circuitry 55 sets readout cycles, the time lengths of readout periods, or the like by using the set reference count numbers.

Next, an example of the typical operation of the photon-counting CT apparatus according to the first embodiment will be described with reference to FIG. 6.

Figure 6:
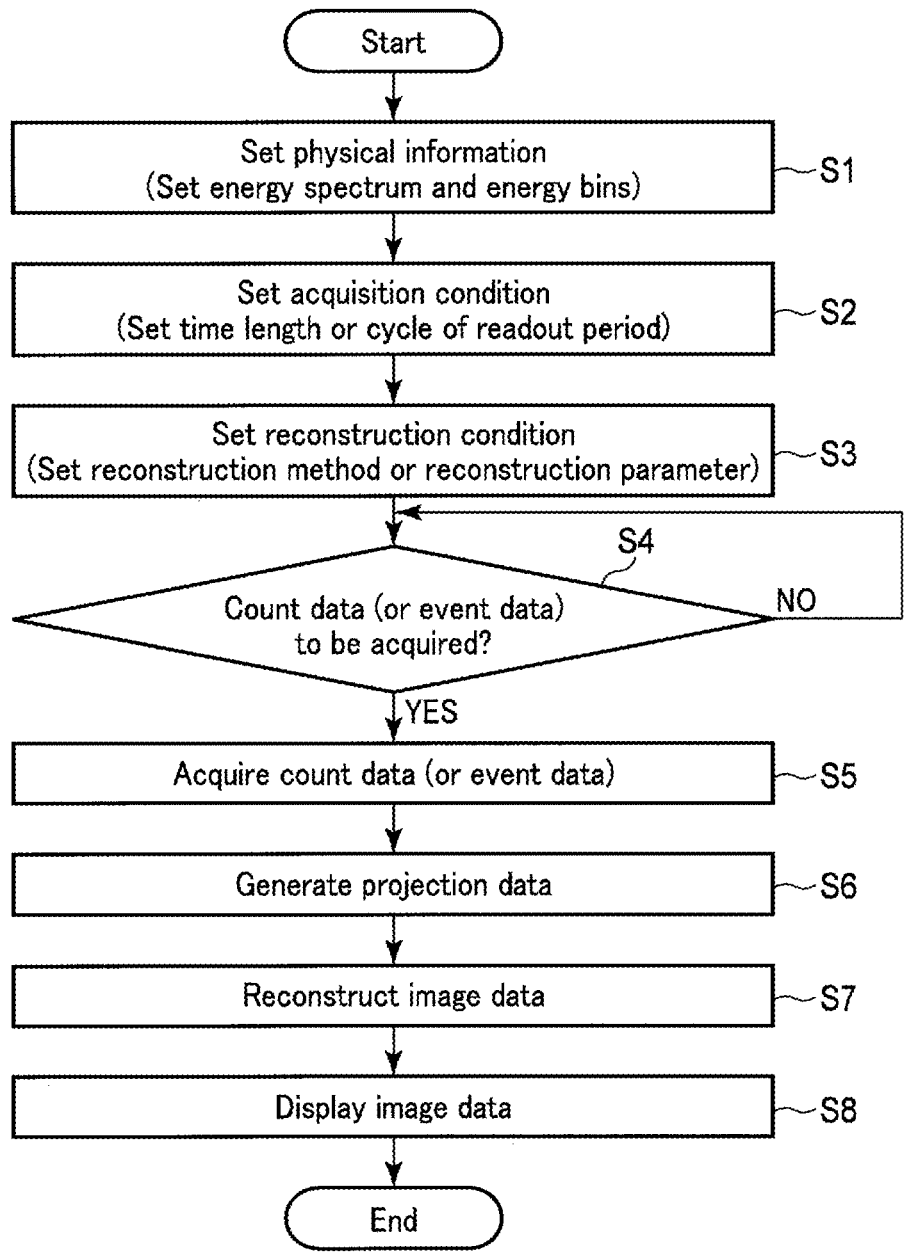
FIG. 6 is a flowchart showing the sequence of a typical operation performed under the control of system control circuitry in FIG. 1 according to the first embodiment.

FIG. 6 is a flowchart showing the sequence of the typical operation performed under the control of the system control circuitry 63 according to the first embodiment. Before a scan, for example, at the time of a scan plan, the system control circuitry 63 causes the setting circuitry 55 to perform setting processing of physical information (step S1). In step S1, the setting circuitry 55 sets physical information such as the energy spectrum (energy distribution) and energy bin of X-ray photons generated by the X-ray tube 13. For example, the setting circuitry 55 sets an energy spectrum in accordance with the material of the anode in the X-ray tube 13, a tube voltage value, and a tube current value. The setting circuitry 55 sets a plurality of energy bins in the set energy spectrum in accordance with, e.g., an instruction from the user. Each energy bin is defined by the energy center value and energy width of the energy bin. The user designates an energy center value and energy width for each energy bin via the operation circuitry 59. The setting circuitry 55 sets an energy bin in accordance with the designated energy center value and energy width. Data of the energy spectrum and energy bin are stored in the main memory circuitry 61.

When step S1 is performed, the system control circuitry 63 causes the setting circuitry 55 to perform processing of an acquisition condition (step S2). In step S2, the setting circuitry 55 sets an acquisition condition such as the time length of a readout period or a readout cycle. More specifically, the setting circuitry 55 sets the time length of a readout period or a readout cycle per unit time based on a reference count number for each of the energy bins set in step S1, as described above. The set time length or cycle of the readout period is stored in the main memory circuitry 61 in association with the energy bin.

When step S2 is performed, the system control circuitry 63 causes the setting circuitry 55 to perform setting processing of reconstruction conditions (step S3). In step S3, the setting circuitry 55 sets reconstruction conditions for each energy bin. The reconstruction conditions include a reconstruction method and a reconstruction parameter.

Figure 7:
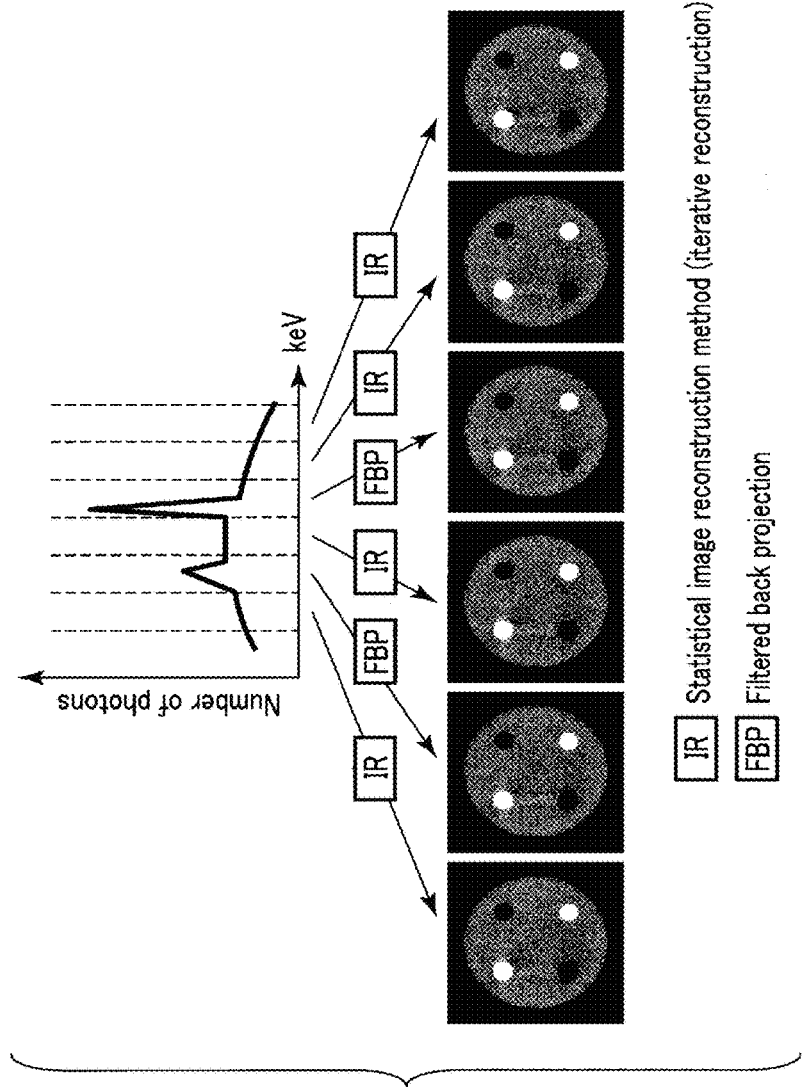
FIG. 7 is a view showing the relationship between the energy bin and a reconstruction method set by the setting circuitry in step S3 of FIG. 5.

FIG. 7 is a view showing the relationship between the reconstruction method and the energy bin. As reconstruction methods in photon-counting CT, a statistical image reconstruction method (IR: Iterative Reconstruction) and an analytical image reconstruction method are known. As the statistical image reconstruction method IR, for example, ML-EM (Maximum Likelihood Expectation Maximization), and OS-EM (Ordered Subset Expectation Maximization) are known. As the analytical image reconstruction method, for example, filtered back projection (FBP) is known. The statistical image reconstruction method has a property in which a relatively high-quality image can be reconstructed using a small number of views. The analytical image reconstruction method has a property in which a high-quality image can be reconstructed in a short time using a sufficient number of views. To the contrary, the analytical image reconstruction method has a property in which the image quality is greatly degraded when the number of views is small. A short readout cycle is set for an energy bin in which the number of incident photons per unit time is large, in comparison with an energy bin in which the number of incident photons per unit time is small. Projection data concerning the energy bin in which the number of incident photons per unit time is large has a larger number of views than in projection data concerning the energy bin in which the number of incident photons per unit time is small.

In consideration of this characteristic of the reconstruction method and the number of views in each energy bin, the setting circuitry 55 sets the analytical image reconstruction method such as FBP for an energy bin in which the number of incident X-ray photons per unit time is large, and the statistical image reconstruction method for an energy bin in which the number of incident X-ray photons per unit time is small. As a result, an appropriate reconstruction method can be set for each energy bin in accordance with the number of views. For each of the plurality of energy bins, a high-quality image can be reconstructed regardless of the number of views. The identifier of the set reconstruction method is stored in the main memory circuitry 61 in association with the identifier of the energy bin.

The reconstruction parameter set by the setting circuitry 55 is, for example, a smoothing parameter for reducing noise of an image. The noise of the image increases/decreases depending on the number of views. More specifically, the noise level of the image rises as the number of views decreases, and drops as the number of views increases. By taking account of this correlation between the number of views and noise, the setting circuitry 55 sets a reconstruction parameter of a relatively low intensity for an energy bin in which the number of incident photons per unit time is large, in comparison with an energy bin in which the number of incident photons per unit time is small. The set reconstruction parameter is stored in the main memory circuitry 61 in association with the identifier of the energy bin.

Note that the waveform of the energy spectrum changes depending on the material of the anode incorporated in the X-ray tube 13. The main memory circuitry 61 may store an LUT (Look Up Table) that associates the waveform of the energy spectrum with the identifier of the energy bin for the identifier of each material of the anode. In this LUT, the time length or cycle of the readout period, the identifier of the reconstruction method, and the reconstruction parameter may be associated with the identifier of each energy bin. When the identifier of the material of the anode installed in the X-ray tube 13 is designated via the operation circuitry 59, the setting circuitry 55 can automatically set, for each energy bin, the time length or cycle of the readout period, the reconstruction method, and the reconstruction parameter that are associated with the designated identifier of the material. This can reduce the labor of setting the time length or cycle of the readout period, the reconstruction method, and the reconstruction parameter for each energy bin.

When step S3 is performed, the system control circuitry 63 waits for input of a count data acquisition start instruction by the user via the operation circuitry 59 or the like (step S4). If preparations for acquiring count data are made, the user inputs a start instruction via the operation circuitry 59 or the like.

In response to the input of the start instruction, the system control circuitry 63 causes the gantry control circuitry 21 to acquire count data (step S5). Also, the system control circuitry 63 transmits, to the gantry control circuitry 21, data of the energy bin, the time length or cycle of the readout period, the reconstruction method, and the reconstruction parameter that have been set in steps S1 to S3.

In step S5, the gantry control circuitry 21 controls the rotation driver 19 to rotate the rotating frame 11 about the rotation axis R at a predetermined angular velocity. During the rotation of the rotating frame 11, the gantry control circuitry 21 controls the high voltage generator 23 to generate X-ray photons from the X-ray tube 13. During the rotation of the rotating frame 11, the gantry control circuitry 21 controls the data acquisition circuitry 25 to generate a count data set in the time length or cycle of a different readout period for each of the plurality of energy bins. The generated count data set is supplied to the projection data generation circuitry 51 of the console 50 via the transmitter 27.

When step S5 is performed, the system control circuitry 63 causes the projection data generation circuitry 51 to perform generation processing of projection data (step S6). In step S6, the projection data generation circuitry 51 performs preprocessing on the count data sets concerning the plurality of energy bins, generating projection data concerning the plurality of energy bins. As the preprocessing, for example, logarithmic transformation is executed. Count data having undergone logarithmic transformation is called projection data. The preprocessing is not limited to only logarithmic transformation, but may include other correction processes such as nonuniformity correction. The other preprocesses are properly applied to count data and projection data. The projection data concerning the plurality of energy bins are stored in the main memory circuitry 61.

Figure 8:
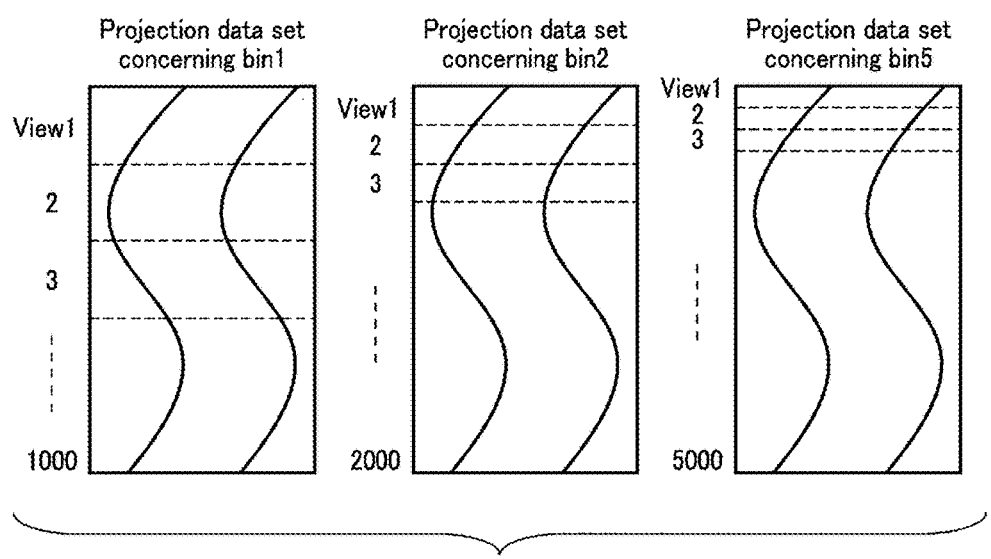
FIG. 8 is a view schematically showing a plurality of projection data sets concerning a plurality of energy bins that are generated by projection data generation circuitry in step S6 of FIG. 5.

FIG. 8 is a view schematically showing a plurality of projection data sets concerning the plurality of energy bins that are generated by the projection data generation circuitry 51. The ordinate of each projection data set is defined as the view, and the abscissa is defined as the channel number. FIG. 8 exemplarily shows a projection data set concerning energy bin 1 (bin1), a projection data set concerning energy bin 2 (bin2), and a projection data set concerning energy bin 5 (bin5) when the readout period is set as shown in FIG. 4B. Each projection data set is a set of projection data by the number of views necessary to reconstruct one image. The number of views necessary to reconstruct one image may be, for example, the number of views included in a period in which the rotating frame 11 rotates by 360°, or the number of views included in a period in which the rotating frame 11 rotates by 180°+fan angle. The projection data set includes the number of views corresponding to the cycle of a readout period set for an energy bin to which the projection data set belongs. As shown in FIG. 4B, the cycle of the readout period of energy bin 2 is ½ of the cycle of the readout period of energy bin 1, that is, the readout frequency of energy bin 2 per unit time is double the readout frequency of energy bin 1. The cycle of the readout period of energy bin 5 is ⅕ of the cycle of the readout period of energy bin 1, that is, the readout frequency of energy bin 5 is five times higher than the readout frequency of energy bin 1. Hence, when the number of views included in a projection data set concerning energy bin 1 is 1,000, the number of views included in a projection data set concerning energy bin 2 is 2,000, and the number of views included in a projection data set concerning energy bin 5 is 5,000.

When step S6 is performed, the system control circuitry 63 causes the reconstruction circuitry 53 to perform reconstruction processing (step S7). In step S7, the reconstruction circuitry 53 performs reconstruction according to the reconstruction method or reconstruction parameter set in step S3. At a stage prior to step S7, the user designates an imaging target energy bin out of the plurality of energy bins via the operation circuitry 59. The reconstruction circuitry 53 applies the reconstruction method or reconstruction parameter set in step S3 to projection data concerning the designated energy bin, and reconstructs image data concerning the designated energy bin. When the user does not designate an energy bin, the reconstruction circuitry 53 may reconstruct image data concerning all the energy bins based on projection data concerning all the energy bins.

When step S7 is performed, the system control circuitry 63 causes the display circuitry 57 to perform display processing (step S8). In step S8, the display circuitry 57 displays, on a display device, the image data reconstructed in step S7. According to this embodiment, the possibility at which an overflow occurs is low in all the energy bins. Thus, the possibility at which an artifact arising from an overflow is generated is low in image data of all the energy bins. In general, even when the number of views included in projection data is relatively small, the possibility at which an artifact is generated in image data is high. According to this embodiment, an appropriate reconstruction method and reconstruction parameter can be set in accordance with the number of views for each energy bin. The possibility at which an artifact arising from a small number of views is generated is low in image data reconstructed by the reconstruction circuitry 53.

The description of the typical operation according to the first embodiment will be ended here.

As described above, the photon-counting CT apparatus according to the first embodiment includes the X-ray tube 13, the X-ray detector 15, the rotating frame 11, the setting circuitry 55, and the data acquisition circuitry 25. The X-ray tube 13 generates X-rays. The X-ray detector 15 repetitively detects X-ray photons generated by the X-ray tube 13, and repetitively generates electrical signals corresponding to the repetitively detected X-ray photons. The rotating frame 11 supports the X-ray tube 13 to be rotatable about the rotation axis R. For each of a plurality of energy bands in X-rays generated by the X-ray tube 13, the setting circuitry 55 sets a readout cycle or the time length of a readout period based on a reference count number in each of a plurality of energy bins. The data acquisition circuitry 25 counts the count number of electrical signals from the X-ray detector 15 for each of the plurality of energy bands in accordance with the set time length or readout cycle.

With this arrangement, the photon-counting CT apparatus according to the first embodiment can set a relatively long time length of the readout period or a relatively long readout cycle for an energy bin in which the reference count number is small, and set a relatively short time length of the readout period or a relatively short readout cycle for an energy bin in which the reference count number is large. The photon-counting CT apparatus according to the first embodiment can substantially uniform count numbers in each readout period throughout the plurality of energy bins.

According to the first embodiment, the time length or cycle of a readout period suited to each energy bin is set for each of the plurality of energy bins, thereby reducing the overflow generation probability while ensuring the number of photons suited to each energy bin.

(Modification)

In the above-described embodiment, the photon-counting apparatus is an X-ray CT type apparatus (photon-counting CT apparatus). However, the photon-counting apparatus according to this embodiment may be an X-ray imaging type apparatus (photon-counting XR apparatus). A modification of the first embodiment will be explained below. Note that the same reference numerals in the following description denote constituent elements having almost the same functions as those in the first embodiment, and a repetitive description will be made only when required.

Figure 9:
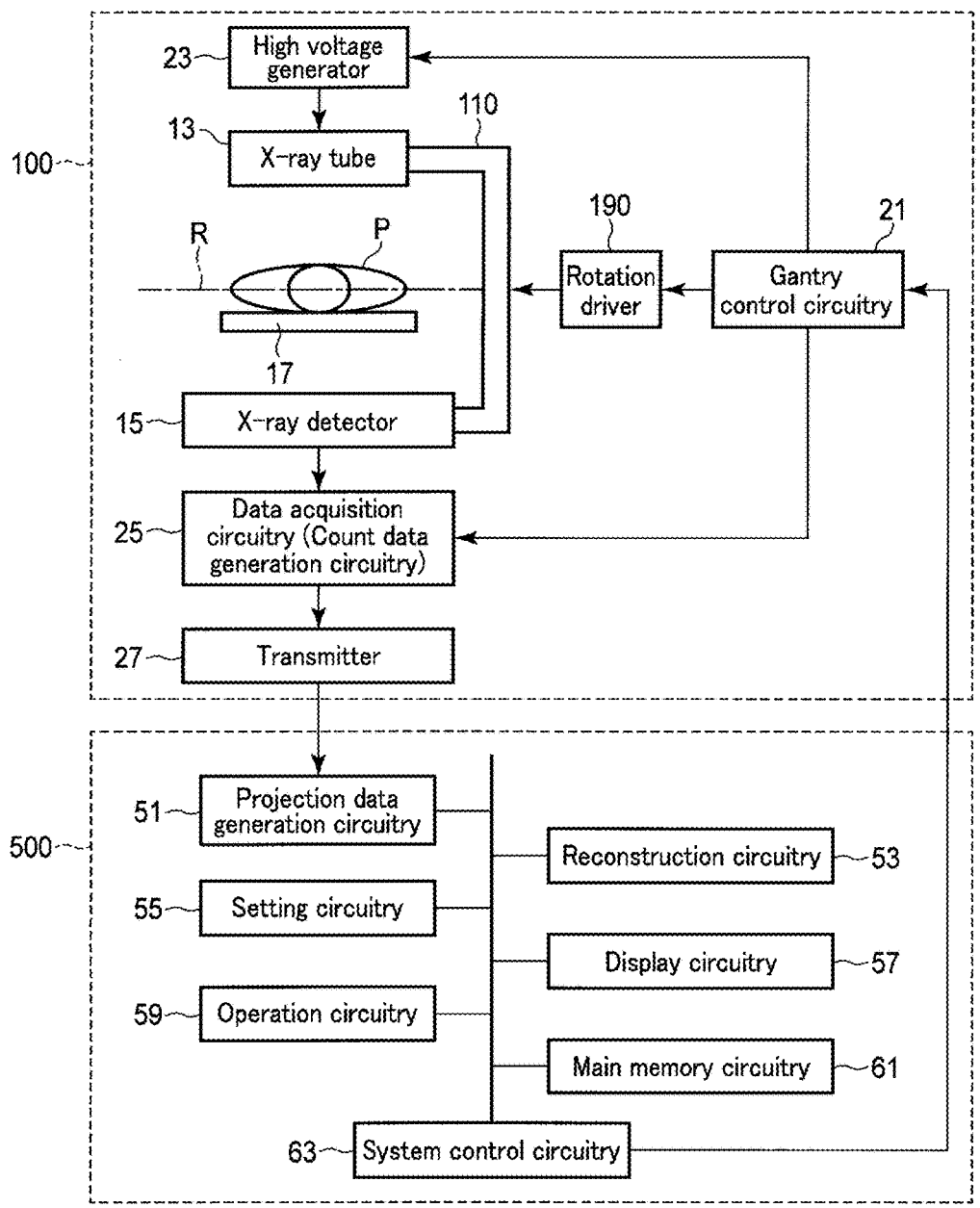
FIG. 9 is a block diagram showing the arrangement of a photon-counting XR apparatus according to a modification of the first embodiment.

FIG. 9 is a block diagram showing the arrangement of a photon-counting XR apparatus according to the modification of the first embodiment. As shown in FIG. 9, the photon-counting XR apparatus according to the modification of the first embodiment includes a gantry 100 and a console 500. The gantry 100 has, e.g., a C-shaped arm 110. The arm 110 supports the X-ray tube 13 and X-ray detector 15 arranged to face each other so that they can rotate about the rotation axis R. The arm 110 receives power from a rotation driver 190 and rotates about the rotation axis R at a predetermined angular velocity. The rotation driver 19 generates power to rotate the rotating frame 11 in accordance with a driving signal from the gantry control circuitry 21.

The gantry control circuitry 21 generally controls various devices included in the gantry 100 in accordance with an instruction from the system control circuitry 63 in the console 500. For example, the gantry control circuitry 21 controls the rotation driver 190, the high voltage generator 23, and the data acquisition circuitry 25. More specifically, the gantry control circuitry 21 controls the rotation driver 190 to rotate the arm 110 at a predetermined angular velocity. The gantry control circuitry 21 controls the high voltage generator 23 to generate X-rays corresponding to predetermined X-ray conditions from the X-ray tube 13. The gantry control circuitry 21 controls the data acquisition circuitry 25 to acquire count data. More specifically, as in the first embodiment, the gantry control circuitry 21 controls the data acquisition circuitry 25 to acquire count data for each of a plurality of energy bins in accordance with a time length or cycle set by the setting circuitry 55 for each of the plurality of energy bins.

With this arrangement, the photon-counting XR apparatus according to the modification of the first embodiment can set a relatively long time length of the readout period or a relatively long readout cycle for an energy bin in which the number of incident photons per unit time is small, and set a relatively short time length of the readout period or a relatively short readout cycle for an energy bin in which the reference count number is large. The photon-counting CT apparatus according to the modification of the first embodiment can substantially uniform count numbers in each readout period throughout the plurality of energy bins.

According to the modification of the first embodiment, the time length or cycle of a readout period suited to each energy bin is set for each of the plurality of energy bins, thereby reducing the overflow generation probability while ensuring the number of photons suited to each energy bin.

(Second Embodiment)

A photon-counting CT apparatus that operates in the list mode will be described below. Note that the same reference numerals in the following description denote constituent elements having almost the same functions as those in the first embodiment, and a repetitive description will be made only when required.

FIG. 10 is a block diagram showing the arrangement of a photon-counting CT apparatus according to the second embodiment.

As shown in FIG. 10, the photon-counting CT apparatus according to the second embodiment includes a gantry 10 and a console 50. The gantry 10 includes data acquisition circuitry 29 for generating event data, instead of the data acquisition circuitry for generating count data in the first embodiment. The console 50 includes projection data generation circuitry 65 that generates projection data based on event data, instead of the projection data generation circuitry that generates projection data based on count data in the first embodiment.

Figures 11, 12:
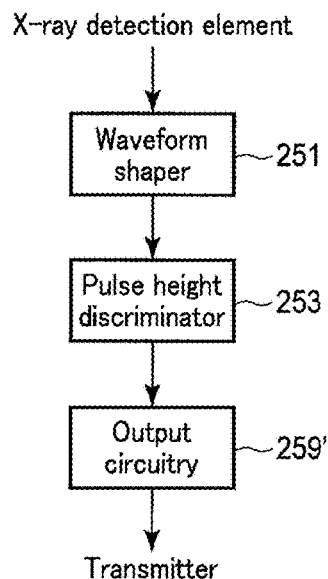
FIG. 11 is a block diagram showing an example of the arrangement of one channel of data acquisition circuitry in FIG. 10.
FIG. 12 is a table showing an example of event data generated by the data acquisition circuitry in FIG. 10.

The data acquisition circuitry 29 generates event data representing the energy and detection time of X-ray photons detected by an X-ray detector 15, for each incident event in accordance with an electrical pulse from the X-ray detector 15. More specifically, the data acquisition circuitry 29 has readout channels by the number of channels corresponding to the number of X-ray detection elements mounted in the X-ray detector 15. The plurality of readout channels are parallelly implemented on an integrated circuit such as an ASIC. FIG. 11 is a block diagram showing an example of the arrangement of one channel of the data acquisition circuitry 29. As shown in FIG. 11, the data acquisition circuitry 29 includes, for each of the plurality of readout channels, a waveform shaper 251, a pulse height discriminator 253, and output circuitry 259'. The waveform shaper 251, the pulse height discriminator 253, and the output circuitry 259' are implemented on an integrated circuit such as an ASIC.

The waveform shaper 251 shapes the waveform of an electrical pulse from the X-ray detection element. The pulse height discriminator 253 is connected to the waveform shaper 251. The pulse height discriminator 253 discriminates, by threshold processing, the peak value of an electrical pulse from the waveform shaper 251, i.e., the energy of X-ray photons detected by the X-ray detection element. More specifically, when the peak value of an electrical pulse from the waveform shaper 251 is a peak value corresponding to an energy bin X, the pulse height discriminator 253 outputs an electrical pulse corresponding to the energy bin X. The output circuitry 259' is connected to the pulse height discriminator 253.

The output circuitry 259' generates event data concerning an incident event for each electrical pulse from the pulse height discriminator 253. The event data includes a record generated for each incident event.

FIG. 12 is a table showing an example of event data. As shown in FIG. 12, event data includes, for each incident event, a record that associates detection time [t], an energy value [E], a channel number [Ch], and a row number [row] with each other. The incident event is an event that X-ray photons have entered the X-ray detection element. The detection time is defined by the time when an electrical pulse was input to the output circuitry 259', in other words, the time when X-ray photons were detected by the X-ray detection element. The energy value is defined by the peak value of an electrical pulse specified by the pulse height discriminator 253, in other words, the typical energy value of an energy bin. In other words, the energy value corresponds to the energy value of X-ray photons originating from an electrical pulse. The typical energy value of an energy bin is set at, e.g., the energy center value, minimum value, or maximum value of each energy bin. The channel number is the channel number of an X-ray detection element that detected X-ray photons. The row number is the row number of the X-ray detection element that detected X-ray photons. For example, a record concerning event 1 in FIG. 12 includes detection time t1, an energy value E1, a channel number Ch1, and a row number row1. Every time an electrical pulse is input from the pulse height discriminator 253, the output circuitry 259' repetitively generates a record concerning an incident event originating from the electrical pulse. The event data (record) is instantaneously transmitted to the console 50 via a transmitter 27.

Next, the arrangement and operation of the projection data generation circuitry 65 will be explained. The projection data generation circuitry 65 retrospectively generates projection data from event data. For each of a plurality of energy bins, the projection data generation circuitry 65 classifies event data into time-series views corresponding to a readout period having a time length or cycle set by setting circuitry 55, and generates projection data based on the classified event data. FIG. 13 is a block diagram showing the arrangement of the projection data generation circuitry 65. As shown in FIG. 13, the projection data generation circuitry 65 includes classification circuitry 651, memory circuitry (temporary memory circuitry) 653, readout control circuitry 655, counting circuitry 657, and preprocessing circuitry 659.

The plurality of memory circuitry 653 corresponding to the respective energy bins are connected to the classification circuitry 651. The classification circuitry 651 classifies event data transmitted from the gantry 10 into the plurality of memory circuitry 653 in accordance with energy values indicated by the event data. Event data are instantaneously transmitted from the gantry 10 to the classification circuitry 651 in the detection time order. More specifically, the classification circuitry 651 specifies the identifier of an energy bin included in event data, and supplies the event data to the memory circuitry 653 corresponding to the energy bin. For example, when event data concerning energy bin 2 is transmitted, the classification circuitry 651 supplies the event data to the memory circuitry 653-2 corresponding to energy bin 2. In this manner, the classification circuitry 651 classifies event data into the plurality of energy bins.

Each memory circuitry 653 temporarily stores event data from the classification circuitry 651 in an internal memory. The memory circuitry 653 reads out event data stored in the memory circuitry 653 in accordance with a readout period having a time length or cycle under the control of the readout control circuitry 655.

The internal memory of the memory circuitry 653 has the upper limit of the capacity for event data. A case will be examined, in which readout is performed at the same timing for all memory circuitry concerning a plurality of energy bins, as in the related art. When the cycle of the readout period is relatively short, a satisfactory event number (count number) cannot be obtained for an energy bin in which the number of incident photons per unit time is small, like energy bin 1, and this may cause an image artifact. When the cycle of the readout period is relatively long, the capacity of the memory circuitry reaches the upper limit value for an energy bin in which the number of incident photons per unit time is large, like energy bin 5, and an overflow (counting loss) occurs.

In this embodiment, the setting circuitry 55 sets the time length or cycle of the readout period for event data from the memory circuitry 653 in accordance with a reference count number in each energy bin. Note that the method of setting the time length or cycle of the readout period by the setting circuitry 55 according to the second embodiment is the same as that in the first embodiment, and a description thereof will not be repeated.

Next, the operation of the readout control circuitry 655 when the cycle of the readout period is set under the condition that the time length of the view and that of the readout period are equal will be explained. In this case, the readout control circuitry 655 transmits a readout trigger to the memory circuitry 653 corresponding to each of the plurality of energy bins in accordance with the cycle of a readout period set by the setting circuitry 55 for this energy bin. In response to receiving the readout trigger from the readout control circuitry 655, each memory circuitry 653 starts write of event data supplied from the classification circuitry 651 in the internal memory. Every time event data is supplied, the memory circuitry 653 writes it in the internal memory. In response to receiving the next readout trigger, the memory circuitry 653 reads out event data concerning a plurality of incident events written in the internal memory, and erases the data written in the internal memory. The memory circuitry 653 starts again write of event data supplied from the classification circuitry 651 in the internal memory. When the cycle of the readout period is set, as shown in FIG. 4B, the memory circuitry 653-5 corresponding to energy bin 5 performs readout of event data at a speed five times higher than that of the memory circuitry 653-1 corresponding to energy bin 1. In this fashion, the memory circuitry 653 reads out event data in each view for each of the plurality of energy bins. Event data in each view will be called an event data set. That is, the memory circuitry 653 repetitively generates an event data set in every cycle (view) of the readout period. The event data set is supplied to the counting circuitry 657.

The operation of the readout control circuitry 655 when the time length of the readout period is set independently of the view will be explained. In this case, the readout control circuitry 655 transmits a readout trigger to the memory circuitry 653 corresponding to each of the plurality of energy bins in accordance with the cycle of a readout period set by the setting circuitry 55 for this energy bin. In response to receiving the readout trigger from the readout control circuitry 655, each memory circuitry 653 starts write of event data supplied from the classification circuitry 651 in the internal memory. In response to the lapse of the readout period, the memory circuitry 653 ends write of the event data in the internal memory. Every time event data is supplied, the memory circuitry 653 writes it in the internal memory. In response to the lapse of the readout period or receiving the next readout trigger, the memory circuitry 653 reads out event data concerning a plurality of incident events written in the internal memory, and erases the data written in the internal memory. The memory circuitry 653 starts again write of event data supplied from the classification circuitry 651 in the internal memory. The event data set is supplied to the counting circuitry 657.

The counting circuitry 657 generates a count data set of each view based on a plurality of event data sets from the memory circuitry 653 for each of the plurality of energy bins. More specifically, the counting circuitry 657 classifies records included in each event data set for each combination of a channel number and row number, and counts the number of records for each combination of the channel number and row number. The number of records for each combination of a channel number and row number corresponds to the number of X-ray photons, i.e., the number of incident events detected in a view by an X-ray detection element at coordinates corresponding to this combination. The counting circuitry 657 generates a count data set by repeating this classification processing for a plurality of event data sets concerning a plurality of views. The count data set is supplied to the preprocessing circuitry 659.

The preprocessing circuitry 659 performs preprocessing on a plurality of count data sets concerning the plurality of energy bins, generating a plurality of projection data sets concerning the plurality of energy bins. As the preprocessing, for example, logarithmic transformation is executed. In logarithmic transformation, the preprocessing circuitry 659 calculates the logarithm of count data for each of the plurality of energy bins. The logarithm of count data is called projection data. Note that the preprocessing is not limited to only logarithmic transformation, but may include other correction processes such as nonuniformity correction. The other preprocesses are properly applied to count data and projection data. The projection data concerning the plurality of energy bins are stored in main memory circuitry 61.

The description of the arrangement and operation of the projection data generation circuitry 65 according to the second embodiment will be ended here.

Even in the second embodiment, event data is acquired by the same sequence as that in the first embodiment shown in FIG. 6. Therefore, the description of the typical operation according to the second embodiment will not be repeated.

In the above description, the photon-counting CT apparatus according to the second embodiment includes an X-ray tube 13, the X-ray detector 15, a rotating frame 11, the data acquisition circuitry 29, the setting circuitry 55, and the projection data generation circuitry 65. The X-ray tube 13 generates X-rays. The X-ray detector 15 repetitively detects X-ray photons generated by the X-ray tube 13, and repetitively generates electrical signals corresponding to the repetitively detected X-ray photons. The rotating frame 11 supports the X-ray tube 13 to be rotatable about the rotation axis R. The data acquisition circuitry 29 generates event data representing the energy and detection time of detected X-ray photons, for each incident event in accordance with an electrical signal from the X-ray detector 15. For each of a plurality of energy bands in the energy spectrum of X-rays generated by the X-ray tube 13, the setting circuitry 55 sets the time length of a readout period or a readout cycle based on a reference count number in each of a plurality of energy bins. For each of the plurality of energy bands, the projection data generation circuitry 65 classifies event data into time-series views in accordance with the set time length or readout period, and generates projection data based on the classified event data.

With this arrangement, the photon-counting CT apparatus according to the second embodiment can set a readout period having a relatively long time length or cycle for an energy bin in which the reference count number is small, and set a readout period having a relatively short time length or cycle for an energy bin in which the reference count number is large. The photon-counting CT apparatus according to the second embodiment can substantially uniform count numbers (event numbers) in each readout period throughout the plurality of energy bins.

According to the second embodiment, a readout period suited to each energy bin is set for each of the plurality of energy bins, thereby reducing the overflow generation probability while ensuring the number of photons suited to each energy bin.

(Modification)

In the above-described embodiment, the photon-counting apparatus is an X-ray CT type apparatus (photon-counting CT apparatus). However, the photon-counting apparatus according to this embodiment may be an X-ray imaging type apparatus (photon-counting XR apparatus). A modification of the second embodiment will be explained below. Note that the same reference numerals in the following description denote constituent elements having almost the same functions as those in the first embodiment, and a repetitive description will be made only when required.

FIG. 14 is a block diagram showing the arrangement of a photon-counting XR apparatus according to the modification of the second embodiment. As shown in FIG. 14, the photon-counting XR apparatus according to the modification of the second embodiment includes a gantry 100 and a console 500. The gantry 100 has, e.g., a C-shaped arm 110. The arm 110 supports the X-ray tube 13 and X-ray detector 15 arranged to face each other so that they can rotate about the rotation axis R. The arm 110 receives power from a rotation driver 190 and rotates about the rotation axis R at a predetermined angular velocity. The rotation driver 19 generates power to rotate the rotating frame 11 in accordance with a driving signal from gantry control circuitry 21.

The gantry control circuitry 21 generally controls various devices included in the gantry 100 in accordance with an instruction from system control circuitry 63 in the console 500. For example, the gantry control circuitry 21 controls the rotation driver 190, the high voltage generator 23, and the data acquisition circuitry 29. More specifically, the gantry control circuitry 21 controls the rotation driver 190 to rotate the arm 110 at a predetermined angular velocity. The gantry control circuitry 21 controls the high voltage generator 23 to generate X-rays corresponding to predetermined X-ray conditions from the X-ray tube 13. The gantry control circuitry 21 controls the data acquisition circuitry 29 to acquire count data. More specifically, as in the second embodiment, the gantry control circuitry 21 controls the data acquisition circuitry 29 to acquire event data for each of a plurality of energy bins.

For each of the plurality of energy bins, the projection data generation circuitry 65 classifies event data into time-series views corresponding to a readout period having a time length or cycle set by the setting circuitry 55, and generates projection data based on the classified event data, as in the second embodiment.

With this arrangement, the photon-counting XR apparatus according to the modification of the second embodiment can set a readout period having a relatively long time length or cycle for an energy bin in which the reference count number is small, and set a readout period having a relatively short time length or cycle for an energy bin in which the reference count number is large. The photon-counting CT apparatus according to the modification of the second embodiment can substantially uniform count numbers in each readout period throughout the plurality of energy bins.

With this arrangement, the photon-counting XR apparatus according to the modification of the second embodiment can set a readout period having a relatively long time length or cycle for an energy bin in which the reference count number is small, and set a readout period having a relatively short time length or cycle for an energy bin in which the reference count number is large. The photon-counting XR apparatus according to the modification of the second embodiment can substantially uniform count numbers (event numbers) in each readout period throughout the plurality of energy bins.

According to the modification of the second embodiment, a readout period suited to each energy bin is set for each of the plurality of energy bins, thereby reducing the overflow generation probability while ensuring the number of photons suited to each energy bin.

Although the modification of the second embodiment has explained a form in which imaging is performed while rotating the arm 110, a form in which imaging is performed while fixing the arm 110 is also possible. In this case, imaging is possible while fixing the angle of the X-ray tube 13 about the rotation axis R and the relative position of the X-ray tube 13 with respect to a top 17 or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A photon-counting apparatus comprising:
an X-ray tube configured to generate an X-ray;
an X-ray detector configured to repetitively detect an X-ray photon generated by the X-ray tube, and repetitively generate an electrical signal corresponding to the repetitively detected X-ray photon;
a support mechanism configured to support the X-ray tube to be rotatable about a rotation axis;
setting circuitry configured to set one of a time length of a readout period and a readout cycle per unit time for the electrical signal based on a reference count number for each of a plurality of energy bands concerning X-rays generated from the X-ray tube; and
data acquisition circuitry configured to count a count number of electrical signals from the X-ray detector in accordance with the set one of the time length and readout cycle for each of the plurality of energy bands,
wherein the setting circuitry sets the time length of the readout period to be a time length corresponding to a time length of a view.

2. The photon-counting apparatus of claim 1, further comprising:
projection data generation circuitry configured to generate projection data based on the count number for each of the plurality of energy bands; and
reconstruction circuitry configured to reconstruct image data based on the projection data concerning a predetermined energy band out of the plurality of energy bands.

3. The photon-counting apparatus of claim 1, wherein the data acquisition circuitry includes an internal memory which stores the count number, and
the setting circuitry sets the readout cycle for an energy band in which the reference count number is larger than an upper limit value of the count number stored in the internal memory, to have a value smaller than a value of the readout cycle for an energy band in which the reference count number is smaller than the upper limit value.

4. The photon-counting apparatus of claim 1, wherein the data acquisition circuitry includes an internal memory which stores the count number, and
the setting circuitry sets the time length of the readout period for an energy band in which the reference count number is larger than an upper limit value of the count number stored in the internal memory, to have a value smaller than a value of the time length of the readout period for an energy band in which the reference count number is smaller than the upper limit value.

5. The photon-counting apparatus of claim 2, wherein the setting circuitry sets a reconstruction method for each of the plurality of energy bands, and
the reconstruction circuitry reconstructs the image data by using a reconstruction method set for the predetermined energy band.

6. The photon-counting apparatus of claim 1, wherein the data acquisition circuitry includes an internal memory which stores the count number, and
the setting circuitry sets an analytical image reconstruction method for an energy band in which the reference count number is larger than an upper limit value of the count number stored in the internal memory, out of the plurality of energy bands, and sets a statistical image reconstruction method for an energy band in which the reference count number is smaller than the upper limit value, out of the plurality of energy bands.

7. The photon-counting apparatus of claim 2, wherein the setting circuitry sets a reconstruction parameter for each of the plurality of energy bands, and
the reconstruction circuitry reconstructs the image data by using a reconstruction parameter set for the predetermined energy band.

8. The photon-counting apparatus of claim 1, wherein the setting circuitry sets the reference count number concerning each of the plurality of energy bands, based on a count number acquired by the data acquisition circuitry in scout imaging preceding a target scan.

9. The photon-counting apparatus of claim 1, wherein the setting circuitry sets the reference count number concerning each of the plurality of energy bands, based on a count number concerning a view of a predetermined ordinal number that has been acquired by the data acquisition circuitry in a target scan.

10. The photon-counting apparatus of claim 1, further comprising a storage unit configured to store, for one of each imaging region and each imaging substance, candidate values of the reference count number concerning each of the plurality of energy bands,
wherein the setting circuitry sets, in the reference count number, a candidate value concerning one of an imaging region and imaging substance designated by a user, out of the candidate values stored in the storage unit.

11. A photon-counting apparatus comprising:
an X-ray tube configured to generate an X-ray;
an X-ray detector configured to repetitively detect an X-ray photon generated by the X-ray tube, and repetitively generate an electrical signal corresponding to the repetitively detected X-ray photon;
a support mechanism configured to support the X-ray tube to be rotatable about a rotation axis;
data acquisition circuitry configured to generate, for each event indicating that the X-ray photons have entered the X-ray detector, event data representing energy and detection time of the detected X-ray photon in accordance with the electrical signal from the X-ray detector;
setting circuitry configured to set, for each of a plurality of energy bands in X-rays generated from the X-ray tube, one of a time length of a readout period and a readout cycle per unit time for the electrical signal based on a reference count number in each of the plurality of energy bands; and
projection data generation circuitry configured to classify the event data into time-series views in accordance with the set one of the time length and readout cycle for each of the plurality of energy bands, and generate projection data based on the classified event data,
wherein the projection data generation circuitry includes an internal memory which stores an event number indicating a number of event data, and
the setting circuitry sets the readout cycle for an energy band in which the reference count number is larger than an upper limit of the event number stored in the internal memory, to have a value smaller than a value of the readout cycle for an energy band in which the reference count number is smaller than the upper limit value.

12. The photon-counting apparatus of claim 11, further comprising reconstruction circuitry configured to reconstruct image data based on projection data concerning a predetermined energy band out of the plurality of energy bands.

13. The photon-counting apparatus of claim 12, wherein the setting circuitry sets a reconstruction method for each of the plurality of energy bands, and
the reconstruction circuitry reconstructs the image data by using a reconstruction method set for the predetermined energy band.

14. The photon-counting apparatus of claim 13, wherein the setting circuitry sets an analytical image reconstruction method for an energy band in which the reference count number is larger than the upper limit value, out of the plurality of energy bands, and sets a statistical image reconstruction method for an energy band in which the reference count number is smaller than the upper limit value, out of the plurality of energy bands.

15. The photon-counting apparatus of claim 12, wherein the setting circuitry sets a reconstruction parameter for each of the plurality of energy bands, and
the reconstruction circuitry reconstructs the image data by using a reconstruction parameter set for the predetermined energy band.

16. A photon-counting apparatus comprising:
an X-ray tube configured to generate an X-ray;
an X-ray detector configured to repetitively detect an X-ray photon generated by the X-ray tube, and repetitively generate an electrical signal corresponding to the repetitively detected X-ray photon;
a support mechanism configured to support the X-ray tube to be rotatable about a rotation axis;
setting circuitry configured to set one of a time length of a readout period and a readout cycle per unit time for the electrical signal based on a reference count number for each of a plurality of energy bands concerning X-rays generated from the X-ray tube; and
data acquisition circuitry configured to count a count number of electrical signals from the X-ray detector in accordance with the set one of the time length of the readout period and readout cycle for each of the plurality of energy bands,
wherein the setting circuitry sets the time length of the readout period to have a value smaller than a value of a time length of a view.

* * * * *